United States Patent [19]

Masamune

[11] Patent Number: 4,644,075

[45] Date of Patent: Feb. 17, 1987

[54] CHIRAL BORANE REAGENTS

[75] Inventor: Satoru Masamune, Newton, Mass.

[73] Assignee: Massachusetts Institute of Technology, Cambridge, Mass.

[21] Appl. No.: 807,096

[22] Filed: Dec. 9, 1985

[51] Int. Cl.[4] .............................. C07F 7/08; C07F 5/02
[52] U.S. Cl. ........................................ 556/403; 568/1; 568/3
[58] Field of Search ........................ 556/403; 568/1, 3

[56] References Cited

U.S. PATENT DOCUMENTS 4,537,773 8/1985 Shenvi ............................ 556/403 X Primary Examiner—Paul F. Shaver
Attorney, Agent, or Firm—Paul J. Cook

[57] ABSTRACT

Chiral borane reagents and their organosilicon derivatives are disclosed.

17 Claims, No Drawings

CHIRAL BORANE REAGENTS

BACKGROUND OF THE INVENTION

The government has rights in this invention under Grant No. NIH-5-RO1-GM33039-02 from the National Institute of Health and under IPA-0010.

This invention relates to novel chiral borane reagents, their method of preparation, and their use in performing asymmetric reactions including hydroboration, ketone reduction, aldol condensation, nucleophilic carbonyl addition, and the Diels-Alder reaction.

Double asymmetric synthesis concerns the interaction of two homochiral reactants, a substrate and a reagent. Evidence has accumulated to show that the ratio of the diastereomeric products resulting through a process of double asymmetric snythesis can be approximated to be (a×b) or (a÷b) where a and b represent the diastereofacial selectivities (D.S.) of the two chiral reactants, respectively. When one of the chiral reactants is replaced by an achiral model reactant in this reaction, the resulting product ratio, a or b, is referred to as the diastereofacial selectivity of the chiral reactant which is not replaced. Thus, a and b represent the extent (and directionality) of a single asymmetric induction. If the two chiral reactants act in concert to enhance the stereoselectivity of the double asymmetric reaction to a×b, then they constitute a matched pair. If not, they are called a mismatched pair and the selectivity is reduced to a÷b. A corollary of this multiplicativity rule which is now established bears a signigicant consequence: A chiral reagent with a large D.S. which can be, and has been devised, is capable of augmenting or overriding the D.S. of a preselected substrate to such an extent that even in a mismatched case, the stereoselectivity of a (double symmetric) reaction is brought to a synthetically meaningful value (for example, 20:1). In order to achieve this controlled high selection, the D.S. of a reagent must be in the order of 100:1 with a substrate with a D.S. of 5:1 or less. This demand has been met for several major organic reactions such as the aldol reaction. The Diels-Alder reaction, and the epoxidation of allylic alcohols, and the strategy of reagent controlled organic synthesis (as opposed to the traditional substrate controlled organic synthesis) has been successfully applied to the synthesis of stereochemically complex natural products. The syntheses of 6-deoxyerythronolide B and many others described in Masamune et al., *Angew Chem. Int. Ed. Engl.*, 1985, 24, pg. 1, amply illustrate this strategy.

In designing chiral boron reagents which are capable of mediating several organic reactions, it is appropriate to start with hydroboration, a reaction that plays an important role in achieving many organic transformations. Thus, hydroboration followed by oxidation, amination, protonolysis, and many other reactions constitute a means of providing alcohols, amines, alkanes (from alkenes), and others normally with high efficiency, and regio- and stereoselection. An asymmetric version of this hydroboration began in 1961 with the discovery of the chiral reagent, diisopinocampheylborane (Ipc$_2$BH), Brown et al., *J. Am. Chem. Soc.*, 1961, 83, 486, and thus far this compound and three other reagents, dilongifolylborane, (Lgf$_2$BH), Jadhav et al., *J. Org. Chem.*, 1981, 46, 2988, limonylborane (LimBH), Jadhav et al., *Heterocycles*, 1982, 18, 169, monoisopinocampheylborane (IpcBH$_2$), Brown et al., *Synthesis*, 1978. 146, have been examined to find the degree of single asymmetric induction. Since the mutual interactions between a prochiral olefin and a chiral reagent effect asymmetric induction, each of the above reagents with four types of olefins has been evaluated: Type I, 2-methyl-1-alkenes; Type II, Z-disubstituted; Type III, E-disubstituted; and Type IV, trisubstituted alkenes.

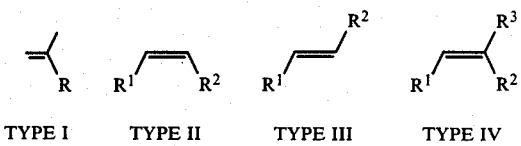

TYPE I    TYPE II    TYPE III    TYPE IV

Both olefins and reagents, each having different steric demands, will induce energy differences due to interaction (mainly steric) in their corresponding diastereomeric transition states, the degree of which will be reflected on the efficiency of asymmetric hydroboration. At the same time, however, large steric interactions may also result in major decreases in reactivity. The steric demand of the olefins increases from Type I to Type IV, while the reagents Ipc$_2$BH, Lgf$_2$BH, LimBH, and IpcBH$_2$ are in decreasing order of the demand. Thus, Ipc$_2$BH, the reagent of largest steric demands, is most favorable for asymmetric hydroboration of Type II olefins with relatively low steric demands. Type II olefins are not handled satisfactorily by any of the other reagents (ee 0–30%). Ipc$_2$BH does not react with either Type III or IV. Both Lgf$_2$BH and LimBH handle three major classes of alkenes, Types II, III, and IV, but with only good but not excellent asymmetric induction (roughly in the neighborhood of 50% ee). IpcBH$_2$, the reagent of lowest steric demands, is capable of hydroborating alkanes of very large steric demands (Type IV) sometimes with high % ee (53–88%). 1-Phenylcyclopentene is an exceptional case (100% ee). However, IpcBH$_2$ fails with Types I and II olefins (1.5–24% ee). Many dialkylboranes resulting from the reaction of IpcBH$_2$ with Type IV olefins are highly crystalline and can be recrystallized to achieve products of essentially 100% optical purity, Brown et al., *J. Am. Chem. Soc.*, 1984, 106, 1797. However, this procedure owes it success to the efficient resolution technique and cannot be applied to either expensive olefins or chiral olefins which must be used in many important chemical transformations.

Accordingly, it would be desirable to provide reagents having a very high diastereofacial selectivity which permits the stereospecific production of organic products in a wide variety of organic reactions.

SUMMARY OF THE INVENTION

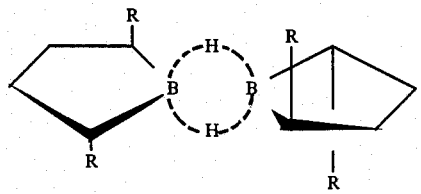

Ia

-continued
SUMMARY OF THE INVENTION

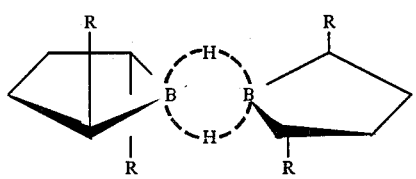  Ib

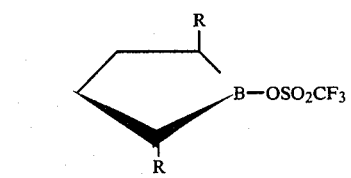  Ic

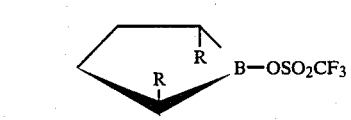  Id wherein R is selected from the group including primary and secondary alkyls and trimethylsilyl.

The chiral borolanes of this invention are capable of converting achiral substrates with enantiomeric excesses averaging about 98%. The effectiveness of these reagents render them useful in performing asymmetric reactions including hydroboration, ketone reduction, aldol condensation, nucleophilic carbonyl addition, and the Diels-Alder reaction.

DESCRIPTION OF SPECIFIC EMBODIMENTS

The compounds of this invention are prepared by a process represented by scheme 1 set forth below (for compounds 2–5, see beginning of examples).

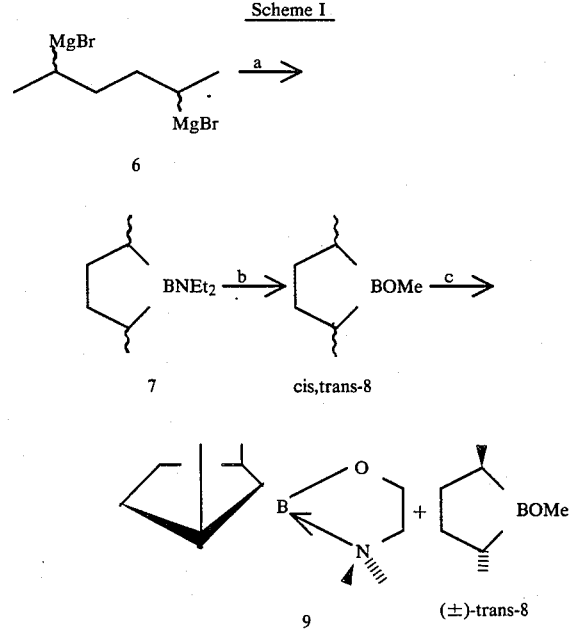

-continued
Scheme I

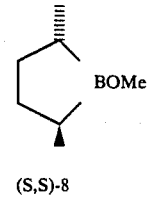

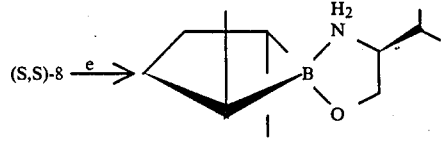

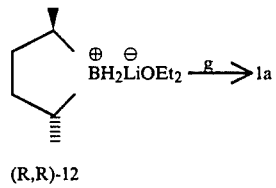

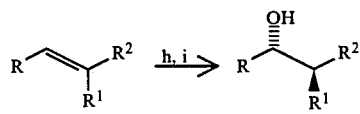

For the case where R is methyl in formulas 1a and 1b, (a) is $Cl_2BNEt_2$, ether THF, $-78°$ C.; (b) HCl/ether, MeOH, pentane, $0°$ C.; (c) $Me_2NCH_2CH_2OH$, pentane, room temperature; (d) (S)-prolinol, pentane, $0°$ C.; (e) (S)-valinol, pentane, $0°$ C.; (f) $LiAlH_4$, MeOH, ether, $0°$ C.; (g) MeI, ether, room temperature; (h) (R,R)-12, MeI, ether, room temperature; (i) $HOCH_2CH_2OH$, 2 or 6N NaOH/MeOH, THF, 30% $H_2O_2$, $40°$–$50°$ C.

For the case where R is ethyl in compounds 1a and 1b, the entire procedure is the same as above except for Step C where $Me_2NCH_2CH_2OH$ is replaced by N-piperidino-2-ethanol (  N—CH₂CH₂OH).

For the case where R is isopropyl (1a' and 1b'), Scheme II is used for their preparations.

Scheme II

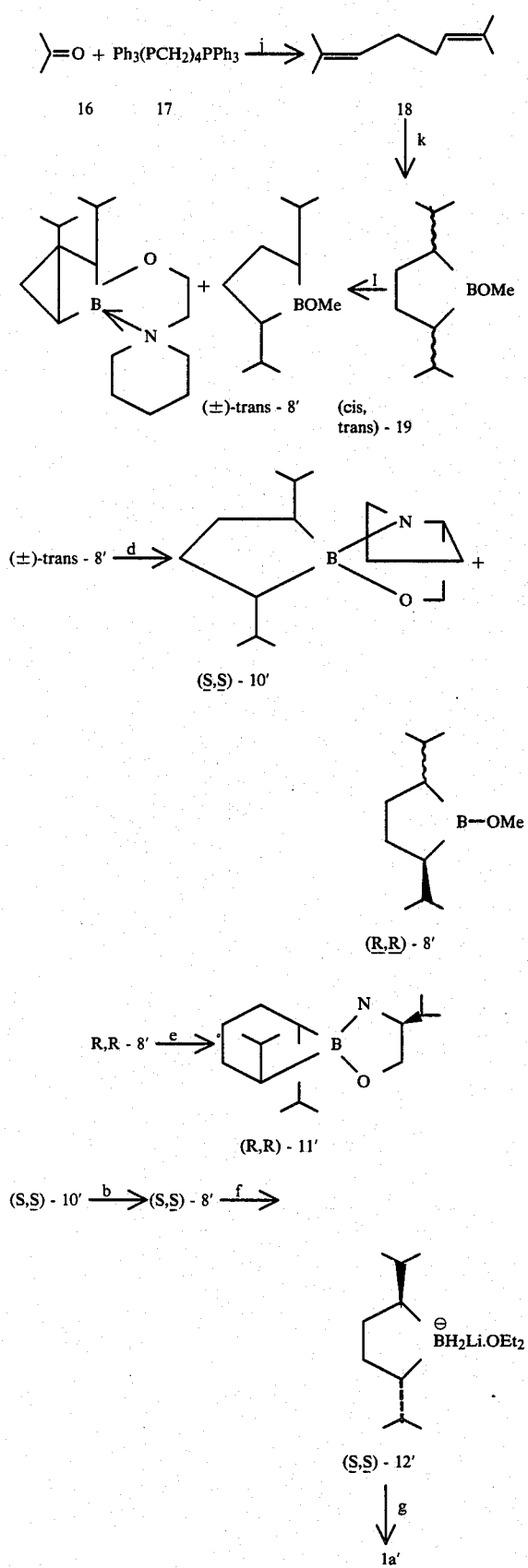

(j) NaH/Me$_2$SO; (k) BH$_3$.THF and then MeOH; (l) N-pyrrolidino-2-ethanol, pentane, $-20°--78°$ C.; (b), (d), (e), (f), (g) are the same as above.

Compounds 1c and 1d are prepared according to Scheme III and outlined below.

Scheme III

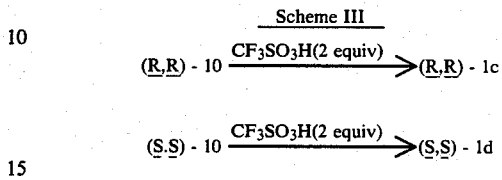

This procedure is general for all 1c and 1d where R=methyl, ethyl, and isopropyl.

In hydroboration, olefins are converted to alcohols in a multi-step procedure (h,i in Scheme I). The borolanes of this invention are added to a solution of the olefin followed by the addition of iodomethane. The resultant composition is heated to a temperature between about 20° and 25° C. for a time of between about 10 and about 20 hours. The solvent is removed and the residue then is dissolved in a suitable solvent such as tetrahydrofuran. Subsequently, a glycol such as ethylene glycol and a methanolic base such as sodium hydroxide together with hydrogen peroxide is added to the solution which is then heated at a temperature between about 40° and 50° C. for about 1 to 5 hours. The alcohol product is recovered by continuous extraction.

In ketone reduction, a ketone is dissolved in a suitable solvent such as pentane and is admixed with the borolane of this invention. A mixture of 30% hydrogen peroxide and 3N NaOH is added to the resultant composition and the corresponding alcohol is extracted by a suitable organic solvent.

In an aldol condensation, a methyl or ethyl ketone is mixed with a B-trifluoromethanesulfoxyborolane (1c and 1d) and diisopropylethylamine and to the resulting boron enolate solution is added an aldehyde at $-78°$ C. After stirring at the same temperature, the resulting composition is treated with 30% hydrogen peroxide at pH 7 and extracted with ether. The organic extracts contain the corresponding aldol product.

In nucleophic carbonyl addition, the reaction is effected as outlined in Scheme IV.

Scheme IV

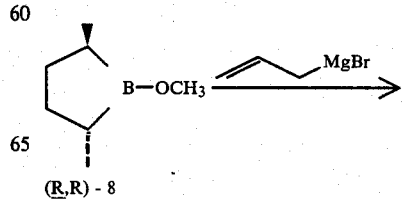

-continued
Scheme IV

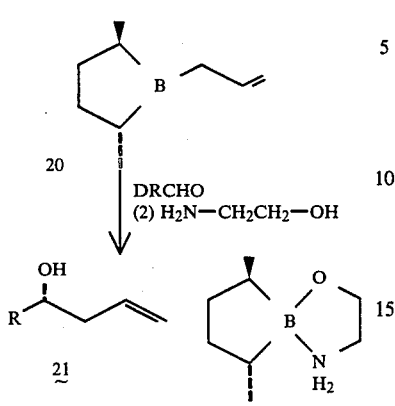

In the Diels-Alder reaction, a dienophile such as maleic anhydride is reacted with a diene such as cyclopentadiene to produce an adduct in the presence of a B-methoxyborolane [(R,R)-8 or (S,S)-8] of this invention. The reaction generally is conducted at a temperature between about −78° to −40° C. for a period of time between about 15 minutes and 1 hour and the adduct is recovered by 1) dilution with ether, washing with a sodium bicarbonate solution, and concentration of the organic layer.

The following examples illustrate the present invention and are not intended to limit the same: In the Table on page 23, compounds 2, 3, 4 and 5 refer to the following compounds:

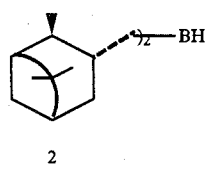

2

Ipc$_2$BH

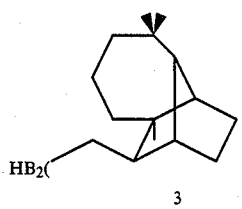

3

Lgf$_2$BH

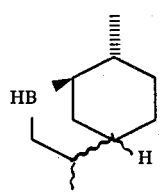

4

LfmBH

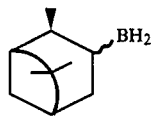

5

IpcBH$_2$

EXAMPLE I

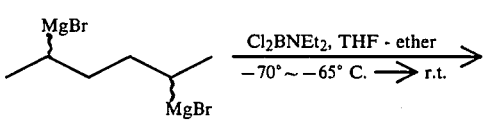

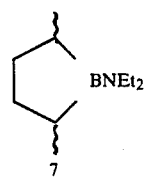

1-(N,N-diethylamino)-2,5-dimethylborolane 7

Dibromoethane (3.0 mL, 0.035 mol) was added to a mechanically stirred suspension of Mg turnings (78 g, 3.21 mol) in THF (160 mL). After 30 min. most of the THF was removed via cannula and fresh THF (270 mL) was added. Then a solution of 2,5-dibromohexane (299 g, 1.24 mol) in THF (650 mL) was added at a rate that maintained the internal temperature at 30°–34° C. The resulting mixture was stirred overnight, filtered through glass wool and diluted with THF to a volume of 2 L. Hydrolysis of an aliquot and titration for total base showed the concentration of this solution to be 0.39M (63% yield, typically 60–65%). The Grignard solution was added to a cooled, magnetically stirred solution of N,N-diethylaminodichloroborane (124 g, 0.80 mol) in ether (1.0 L) at a rate that allowed maintenance of an internal temperature of −70° to −65° C. The resulting suspension was allowed to warm to 20° C. overnight. The solids were allowed to settle and the supernatant was removed via cannula. The solids were washed with pentane (four times) and the combined supernatants were concentrated by fractional distillation. The residue was vacuum transferred to a cold (dry ice-acetone) receiver by heating the residue to 120° C. at 0.1 torr. Distillation under reduced pressure gave the diethylaminoborolane 7 as a mixture of isomers (72.8 g, 0.44 mol) in 56% yield. On a small scale yields up to 70% were obtained.

bp 79°–82° C. (15 torr); $^1$H NMR $\delta$0.83(3H, d, J=7.7 Hz), 0.93(3H, d, J=7.2 Hz), 1.04(6H, d of t, J=1.0, 7.2 Hz), 1.05–1.80(6H, m), 3.0–3.2(4H, m); $^{13}$C NMR $\delta$15.4, 15.6, 22.8, 33.7, 34.2, 42.6; $^{11}$B NMR $\delta$50.

EXAMPLE II

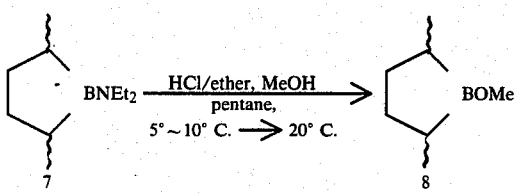

Cis- and trans-1-methoxy-2,5-dimethylborolane 8

A solution of ethereal HCl (234 mL, 0.80 mol) was slowly added to a cooled, mechanically stirred solution of methanol (41.3 mL, 1.02 mol) and diethylaminoborolane 7 (131 g, 0.78 mol) in pentane (1.3 L). The internal temperature was maintained between 5°–10° C. A white precipitate formed during the addtion and the resulting suspension was stirred at 20° C. for 12 h. The solution was filtered, the precipitate washed with pentane and the solvent removed from the filtrate by distillation at atomospheric pressure through a 50 cm Vigreaux column. The residue was distilled under reduced pressure to give methoxyborolane 8 as a colorless oil (85 g, 67 mol, 86% yield, cis:trans ratio 47:53).

bp 49°–52° C. (33 mm). For other physical data see characterization of pure isomers below.

EXAMPLE III

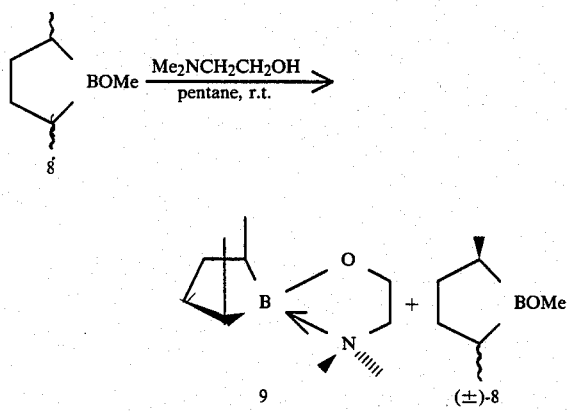

(R,S)-1-(2-N,N-dimethylaminoethoxy)-2,5-dimethylborolane 9 and transmethoxyborolane (±) 8

N,N-dimethylethanolamine (11.5 mL, 114 mmol, 45 mol %) was added to a magnetically stirred solution of cis- and trans-methoxyborolanes 8 (32.0 g, 0.254 mmol) in pentane (220 mL) at room temperature. After 2 h the solution was vacuum transferred to a receiver cooled in dry ice-acetone. The transfer was completed by reducing the pressure to 0.1 torr and heating the reaction flask to 70°–80° C. The white crystalline residue was essentially pure cis complex 9 (21.0 g, 114 mmol, 100%, cis:trans ratio >98:2 by $^1$H NMR). Recrystallization from pentane gave pure 9. The vacuum transferred material was treated with a second portion of dimethylethanolamine (2.1 ml, 21 mmol, 8 mol %). Vacuum transfer as above gave a solid residue (4.2 g, 23 mmol, 109% cis:trans ratio 1:2). The vacuum transferred material was concentrated by distillation at atmospheric pressure. The residue was distilled at reduced pressure to give trans-methoxyborolane (±)-8 (12.9 g, 103 mmol, 86%, cis:trans ratio 2:98).

Data for complex 9 mp 59°–60° C.; $^1$NMR δ 0.55(2H, m), 0.82(6H, d, J=7.3 Hz), 1.1–1.6(4H, m), 2.49(6H, s), 2.85(2H, t, J=7 Hz); $^{13}$C NMR δ 17.0, 23.4, 34.9, 44.6, 59.1, 59.5; $^{11}$B NMR δ 12.8; mass spectrum, m/z (relative intensity), 183 (7), 182(2.4), 140(29), 126(17), 72(44), 58(100).

Data for trans-methoxyborolane (±) 8 bp 51°–54° C. (34 torr); $^1$H NMR δ 0.95(6H, br s), 1.05–1.2(2H, m), 1.8–2.0(4H, m), 3.80(3H, s); $^{13}$C NMR δ 14.0, 24.5, 33.5, 55.1; $^{11}$B NMR δ 57.

EXAMPLE IV

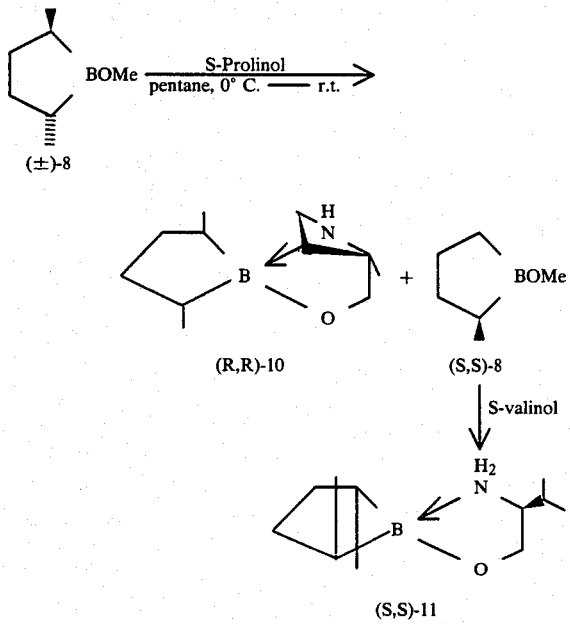

Prolinol complex 10 and valinol complex 11

(S)-(+)-prolinol (4.66 g, 46.1 mmol, 45 mol %) in ether (5 ml) was added dropwise to a magnetically stirred solution of trans-borolane 8 (12.9 g, 102 mmol) in pentane (100 mL) at 0° C. A white precipitate formed during the addition. The suspension was stirred 30 min at 0° C. and 1.5 h at 20° C. The volatile materials were vacuum transferred to a receiver cooled in dry ince-acetone. The transfer was completed by reducing the pressure to 0.1 torr and raising the temperature to 70°–80° C. The white crystalline residue was nearly pure prolinol complex 10 (9.14 g, 46.8 mmol, 102%). Crystallization from CH$_2$Cl$_2$ gave the pure complex.

mp 225°–226° C.; $^1$H NMR δ 0.50–0.70(2H, m), 0.89(6H, d, J=7.2 Hz), 1.7–1. 85(4H, m), 2.0–2.2(2H, m), 2.85–3.2(2H, m), 3.56(1H, dd, J=3.2, 9.2 Hz), 3.60–3.75(1H, m), 3.91(1H, dd, J=6.2, 9.1 Hz), 4.1–4.25(1H, br s); $^{13}$C NMR δ 18.0, 26.0, 27.2, 31.2, 36.6, 48.6, 61.5, 67.4; $^{11}$B NMR δ 11; mass spectrum, m/z (relative intensity), 195(10.4), 194(6.6), 152(73), 139(64), 138(58), 84(50), 70(100); [α]$_D^{21}$+23.2 (c 1.28CHCl$_3$).

The volatile material was treated with a second portion of prolinol (1.02 g, 10.2 mmol, 10 mol %). Vacuum transfer as above gave a 1:1 mixture of prolinol complexes (2.19 g, 11.2 mmol, 110%). The volatile material was treated with (S)-(+)-valinol (4.78 g, 46.3 mmol, 45 mol %) in ether (5 ml). Removal of the volatiles in vacuo (0.1 torr, 80° C.) gave nearly pure valinol complex 11 (8.77 g, 44.6 mmol, 96%). Recrystallization from CH$_2$Cl$_2$-pentane gave the pure complex.

mp 151°-154° C.; $^1$H NMR δ 0.40-0.60(2H, m), 0.88(6H, d, J=7.2 Mz), 96(3H, d, J=7.2 Hz), 1.16(3H, d, J=7.2 Hz), 1.6-1.8(4H, m), 2.8-3.0(1H, m), 3.56(1H, dd, J=9.9 Hz), overlaps 3.45-3.65(2H, br s), 4.00(1H, dd, J=7.9 Hz); $^{13}$C NMR δ 19.0, 20.1, 27.0, 31.0, 36.0, 60.9, 66.4; $^{11}$B NMR δ 12; mass spectrum, m/z (relative intensity) 197(0.7), 170(9.7), 170(9.7), 154(54), 72(100); exact mass calculated for C$_{11}$H$_{24}$BNO, m/z 197.1951, Found 197.1950; [α]$_D^{21}$ −3.33° (c 1.17, CHCl$_3$).

EXAMPLE V

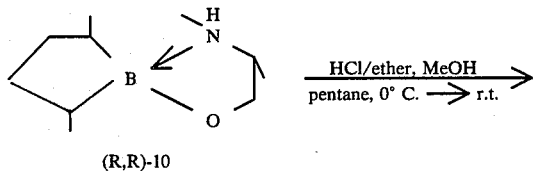

(R,R)-10

(R,R)-8

Synthesis of (R,R)-methoxyborolane 8 from aminoalcohol complex 10

A solution of ethereal HCl (15.4 ml, 18.8 mmol) was added dropwise to a magnetically stirred solution of methanol (0.95 ml, 23 mmol) and prolinol complex 10 (3.50 g, 17.9 mmol) in pentane (50 mL) at 0° C. After 6 h the solution was filtered. The filtrate was concentrated by distillation through a Vigreaux column at atmospheric pressure and the residue was distilled at reduced pressure (60°-61° C., 61-63 mm Hg) to give (R,R)-8 (1.83 g, 81% yield). In a similar manner valinol complex 11 was converted to (S,S)-8 in 70% yield.

EXAMPLE VI

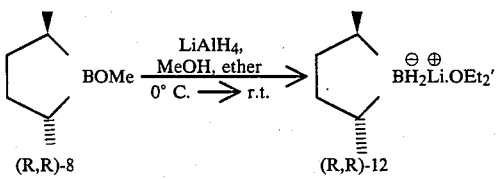

Synthesis of (S,S)- and (R,R)-dihydro-2,5-dimethylboratacyclopentane ethereate 12

An ethereal solution of LiAlH$_4$ (59.8 mL, 14.5 mmol) was slowly added to a magnetically stirred solution of the desired methoxyborolane 8 (1.83 g, 14.5 mmol) in ether (5 mL) at 0° C. A gelatinous precipitate formed during the addition. The solution was warmed to 20° C. and stirred to 1 h. The solution was cooled in an ice bath and methanol (1.06 mL, 26.2 mmol) was added dropwise. After 2 h at 20° C., the solution was filtered. Removal of the solvent in vacuo (20° C., 0.1 torr) gave borohydride 12 as the monoethereate (2.02 g, 78% yield).

$^1$H NMR (C$_6$D$_6$) δ 0.98(6H, t, J=7.2 Mz), 1.26(2H, m), 1.42(6H, d, J=6.8 Mz), 1.55(2H, m), 2.28(4H, m), 3.11(2H, dq, J=6.9, 10.1 Hz), 3.18(2H, dq, J=7.2, 10.1 Hz); $^{13}$C NMR (C$_6$D$_6$) δ 14.4, 22.3, 24.1, 38.9, 66.3; $^{11}$B NMR (C$_6$D$_6$) δ−11.6(t, J=70 Hz).

EXAMPLE VII

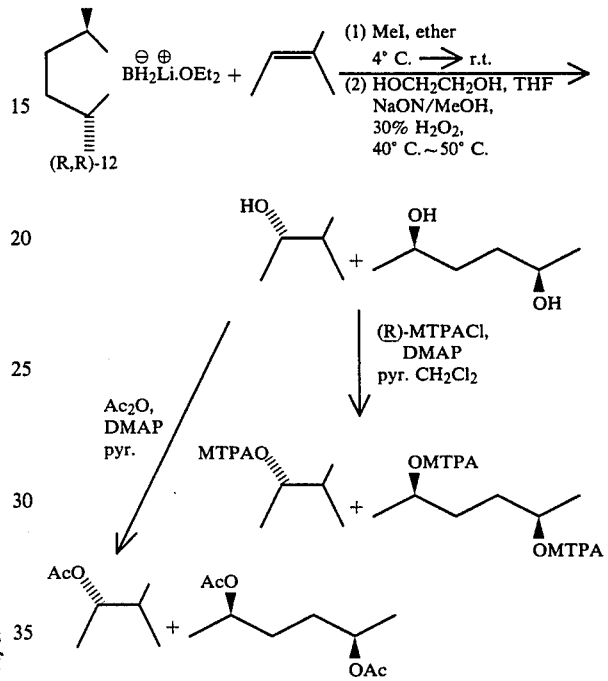

Typical procedure for asymmetric hydroboration of olefins

Borohydride R,R-12 (3.6 mL, 1.8 mmol, 0.50 solution in ether) was added to a solution of 2-methyl-2-butene (1.59 mL, 1.5 mmol) in ether (2 mL) at 4° C. Then iodomethane (0.224 mL, 3.6 mmol) was added. The solution was stirred at 22° C. for 15 h. The solvent was removed in vacuo (50 torr) and the residue was dissolved in THF (1.3 mL). Ethylene glycol (0.2 mL, 3.6 mmol, degassed), methanolic NaOH (2.7 mL, 10.8 mmol, degassed) and 30% H$_2$O$_2$ (0.9 mL, 9 mmol) were added at 4° C. The solution was heated to 40°-50° C. for 2 h. Continuous extraction with pentane (25 mL) gave a solution containing primarily 3-methyl-2-butanol. Continuous extraction with ether (20 mL) gave a solution of 2,5-hexanediol. The residue (ca. 1.5 mL) was diluted with pentane (2.5 ml) and decane (0.100 mL) was added as an internal standard for GC analysis. A portion (0.4 mL) of the pentane solution was acetylated with acetic anhydride (0.5 mL), pyridine (0.5 mL) and 4-dimethylaminopyridine (DMAP) (3 mg). After the usual workup GC analysis showed that the overall yields of 2-acetoxy-3-methylbutane and 2,5-diacetoxyhexane were 90 and 26%, respectively. Chromatography of the remaining pentane solution (ether/pentane, 1:4), concentration at atmospheric pressure and bulb to bulb distillation (320 torr, 80°-100° C. T$_b$) gave 3-methyl-2-butanol (105 mg). The MTPA ester of this alcohol was prepared as follows: A solution of the alcohol (10 mg), DMAP (2 mg), pyridine (1. ml) and (R)-MTPA chloride (0.030 mL) in CH$_2$Cl$_2$ (1 ml) was stirred at 20° C. for 12 h. After the usual workup HPLC analysis of this oil (0.3% ether/hexane, 2 mL/min) showed two peaks in a ratio of 97.1 (t$_R$ 34.5 min) to 2.9 (t$_R$ 32.3 min).

The ether solution from continuous extraction was dried (MgSO$_4$), evaporated and distilled (bulb-to-bulb, 30 torr, 120°–130° C. T$_b$) to give 2,5-hexanediol (161 mg, 76%). The bis-MTPA ester was prepared as above. HPLC analysis (7% ether/hexane, 2 mL/min) showed 95.7% of the MTPA ester of the R,R diol (t$_R$ 18.4 min), 4.3% of the bis-MTPA ester of the R,S diol (t$_R$ 22.1 min) and <0.3% of the bis MTPA ester of the S,S diol (t$_R$ 25.7 min). Thus the ee used to correct the optical purity of the butanol was 95.7.

TABLE I

Asymmetric Hydroboration with Achiral Olefins with 1a, 2, 3, 4, and 5

| | | | | | With 1a of 96.5% or 97.5% ee[a] | | | | % ee of 15 corrected for the enantiomeric purity of each chiral borane used | | | |
|---|---|---|---|---|---|---|---|---|---|---|---|---|
| entry | olefin | olefin type | reaction time, h. (temp.) | alcohol 15 | % yield of 15[b] | $[\alpha]_D^{21}$ of 15[c] | % ee of 15 obtained | 1a | (Ipc)₂BH(2) (config.)[d] | (Lgf)₂BH(3) (config.)[d] | LimBH(4) (config.)[d] | IpcBH₂(5) (config.)[d] |
| 1 | (isopropyl-CH=CH₂) | I | 1 | HOCH₂-CH(iPr)H | 85 | +0.25° (c 1.18, CHCl₃)[f] | 1.4[g] | 1.5 (S) | 32 (R)[h] | | | |
| 2 | | II | 36 (4° C.)[i] 2 | (2-butanol) | 75 | +13.3° (c 0.63, CH₃OH)[j] | 95.2[k] | 97.6 (S) | 99.1 (R) | 78 (R) | 55.0 (R) | 24 (S) |
| 3 | | II | 6.5[e] | (hexan-3-ol) | 83 | +8.86° (c 0.93, C₂H₅OH)[l] | 96.4[m] | 99.4 (S) | 94.1 (R) | 71 (R) | | |
| 4 | | III | 12 (−20° C.)[i] 48 (4° C.) | (pentan-2-ol) | 71 | +13.4° (c 0.71, CH₃OH)[j] | 97.0[k] | 99.5 (S) | 14 (R)[h] | 25 (S) | 58.6 (R) | 73 (S) |
| 5 | | III | 10[e] | (heptan-3-ol) | 83 | +8.83° (c 1.05, C₂H₅OH)[l] | 96.0[m] | 99.5 (S) | | | | 75 (S) |
| 6 | | IV | 15[e] | (3-methylbutan-2-ol) | 90 | +5.04° (c 1.13, C₂H₅OH)[n] | 94.2[k] | 97.6 (S) | 15 (R)[h] | 70 (R) | 66.5 (R) | 53 (S) |
| 7 | | IV | 9.5[e] | (trans-2-methylcyclopentanol) | 89 | +46.6° (c 1.13, CH₃OH)[o] | 97.0[m] | 100 (S,S) | 24 (S,S) | 63 (R,R) | 45.0 (R,R) | 66 (S,S) |
| 8 | | IV | 96[i] | (trans-2-methylcyclohexanol) | 60 (69)[p] | +37.8° (c 1.16, CH₃OH)[q] | 93.2[k] | 95.6 (S,S) | | | | 77 (S,S) |

TABLE I-continued

Asymmetric Hydroboration with Achiral Olefins with 1a, 2, 3, 4, and 5

| | | | With 1a of 96.5% or 97.5% ee[a] | | | | | % ee of 15 corrected for the enantiomeric purity of each chiral borane used | | | |
|---|---|---|---|---|---|---|---|---|---|---|---|
| entry | olefin | olefin type | reaction time, h. (temp.) | alcohol 15 | % yield of 15[b] | $[\alpha]_D^{21}$ of 15[c] | % ee of 15 obtained | 1a | (Ipc)$_2$BH(2) (config.)[d] | (Lgf)$_2$BH(3) (config.)[d] | LimBH(4) (config.)[d] | IpcBH$_2$(5) (config.)[d] |
| 9[e] | (cyclohexylidene-ethylene) | IV | 12 | HO⟋(1-cyclohexylethanol) | 97 | −10.6 (c 1.36, CCl$_4$)[r] | 95.8[k] | 99.3 (S) | | 52 (R) | | |

[a]Reaction in ethyl ether using 1.2 equiv of (R,R)-12 and 2.4 equiv of CH$_3$I at room temperature (21–23° C.) unless otherwise noted.
[b]Determined by GC analysis after acetylation [(CH$_3$CO)$_2$O—C$_5$H$_5$N—4-(CH$_3$)$_2$NC$_5$H$_4$N].
[c]All optical rotations were measured at the alcohol stage except entry 9 (acetate).
[d]Data from Brown's reports (ref 7 and the following: Brown, H. C.; Ayyangar, N. R.; Zweifel, G. J. Am. Chem. Soc. 1964, 86, 1071). All numbers are corrected for the optical purity of the starting material.
[e](R,R)-12 of 96.5% ee was used for hydroboration.
[f]R alcohol $[\alpha]_D^{28}$ −2.95° (c 60.52), CHCl$_3$): Tsuda, K.; Kishida, Y.; Hayatsu, R. J. Am. Chem. Soc. 1960, 82, 3396.
[g]Based on $^1$H NMR of the MTPA ester.
[h](+)-(Ipc)$_2$BH derived from (−)-α-pinene was used.
[i](R,R)-12 of 97.5% ee was used.
[j]Commercially available S alcohol (81.6% ee HPLC analysis of MTPA ester, Aldrich Chemical Co.) $[\alpha]_D^{21}$ +12.0° (c 1.12, CH$_3$OH).
[k]HPLC analysis of the derived MTPA esters: Dale, J. A.; Dull, D. L.; Mosher, H. S. J. Org. Chem. 1969, 34, 2543.
[l]S alcohol $[\alpha]_D^{20}$ +8.0 (c 0.6, C$_2$H$_5$OH): Davies, J.; Jones, J. B. J. Am. Chem. Soc. 1979, 101, 5405.
[m]HPLC analysis of the Pirkle's carbamates: Pirkle, W. H.; Hoekstra, M. S. J. Org. Chem. 1974, 39, 3904.
[n]S alcohol $[\alpha]_D^{25}$ +5.34° (c 5.0, C$_2$H$_5$OH): Pickard, R. H.; Kenyon, J. J. Chem. Soc. 1913, 103, 1923.
[o]1S,2S alcohol $[\alpha]_D^{25}$ +43.9° (c 1.00, CH$_3$OH): Partridge, J. J.; Chadha, N. K.; Uskokovic, M. R. J. Am. Chem. Soc. 1973, 95, 532.
[p]Yield in parenthesis is based on consumed starting material.
[q]1S,2S alcohol $[\alpha]_D^{20}$ +42.9° (c 1, CH$_3$OH): Backstrom, R.; Sjoberg, B. Ark. Kemi 1967, 26, 549.
[r](S)-1-Acetoxy-1-cyclohexylethane of 32 ± 6% ee shows $[\alpha]_D^{25}$ −1.6° (c 1.1, CCl$_4$): This (−)-isomer was erroneously recorded as having an R configuration (personal communication from Professor Meyers): Meyers, A. I.; Ford, M. E. J. Org. Chem. 1976, 41, 1735.

EXAMPLE VIII

Analysis of optical purity of complexes 10, 11, methoxyborolane 8 and borohydride 12

The optical purities of the above compounds were determined as follows: A solution of the appropriate borolane (0.1 mmol) in THF (2 mL) was oxidized by the addition of ethylene glycol (0.012 mL), 2N methanolic NaOH (0.3 mL, 0.6 mmol) and 30% $H_2O_2$ (0.05 mL) followed by heating to 40°–50° C. for 2 h. The solution was cooled, diluted with ether (5 mL) and saturated with anhydrous $K_2CO_3$. The solution was filtered and the filtrate dried over $K_2CO_3$. Filtration and removal of the solvents in vacuo (20° C., 0.1 torr) gave crude 2,5-hexanediol. Treatment with (R)-MTPA chloride (3 equiv) as above gave the bis-MTPA diesters which were analyzed by HPLC. When samples were analyzed at each stage, the effective enantiomeric excesses so determined were in agreement within ±1%.

Our use of the term enantiomeric excess is not, strictly speaking, proper because our calculations include a correction for the presence of the cis isomer. The cis isomer is treated as though it were a 1/1 mixture of the (R,R) and (S,S) compounds. Thus an HPLC analysis showing the presence of 95% (R,R), 4% (R,S) and 1% (S,S) diesters provides an effective ee of (95+2)-(1=2) or 94% ee.

EXAMPLE IX

Determination of Absolute Configurations of complexes 9, 10, 11

A solution of prolinol complex 10 (779 mg, 4.0 mmol) in THF (20 mL) was oxidized as above with ethylene glycol (0.44 mL, 7.9 mmol), 2M methanolic sodium hydroxide (12 mL, 24 mmol) and 30% $H_2O_2$ (2 mL, 20 mmol). Ether (50 mL) was added and the solution was washed with brine (2×10 mL). The aqueous phase was extracted with ether (2×10 mL). The combined organic layers were dried ($K_2CO_3$) and evaporated. Chromatography (ethyl acetate) of the residue afforded (R,R)-2,5-dihydroxyhexane (356 mg, 75% yield). The idol was acetylated with acetic anhdride (1.5 mL) and DMAP (30 mg) at 20° C. for 12 h. Standard workup followed by chromatography (ethylacetate/hexane, 1:9) gave (R,R)-2,5-diacetoxyhexane (482. mg, 80% yield). Bulb-to-bulb distillation gave pure diacetate.

bp 90°–90° C. (4 torr); $[\alpha]_D^{21}+3.00$ (c 8.32, $CHCl_3$); $^1H$ NMR $\delta$ 1.18 (6H, d, J=6.2 Hz), 1.55(4H, m), 2.00(6H, s), 4.86(2H, m); $^{13}C$ NMR $\delta$ 19.8, 21.1, 31.5, 70.4, 170.4.

A solution of this diacetate (349 mg, 1.73 mmol) in THF (5 mL) was added to a suspension of $LiAlH_4$ (131 mg, 3.45 mmol) in THF (10 mL) at 4° C. and stirred for 1 h. Ether (15 mL) was added followed by 1M aq NaOH (0.5 mL) and the insoluble material was removed by filtration. Evaporation gave (R,R)-2,5-dihydroxyhexane (217 mg, 100%). Bulb-to-bulb distillation afforded pure diol. bp 90°–100° C. (4 torr); mp 51°–53° C.; $^1H$ NMR $\delta$ 1.18(6H, d, J=6.1 Hz), 1.54(4H, m) 2.06(2H, s), 3.84(2H, m); $^{13}C$ NMR $\delta$ 23.6, 36.0, 68.2; $[\alpha]_D^{21}-31.9°$ (c 7.38, $CHCl_3$). Serck-Hannsen, K.; Stallberg-Stenhangen, S.; Stenhangen, E. *Ark. Kemi,* 1953,5,203: found $[\alpha]_D^{23}-35.6$ (c 8.29, $CHCl_3$). The bis-MTPA ester of this diol was prepared as above and shown to be a 92% R,R 4% S,S mixture of diesters.

Oxidation and acetylation of the valinol complex gave (S,S)-2,5-diacetoxyhexame (57% yield) identical with the (R,R)-diacetate except for rotation. $[\alpha]_D^{21}-3.27$ (c 7.98, $CHCl_3$). Reduction with LAH gave (S,S)-2,5-dihydroxyhexane (100% yield) identical with (R,R)-diol except for rotation.

$[\alpha]_D^{21}+34.2$ (c 6.82, $CHCl_3$. Serck-Hanssen et al.: found $[\alpha]$ 25+35.1 (c 9.49, $CHCl_3$). The bis MTPA ester was 1% R,R, 3% R,S and 96% S,S.

Oxidation and acetylation of the cis complex gave (R,S)-2,3-diacetoxyhexane (70% yield). bp 80°–90° C. (4 torr); $^1H$ NMR $\delta$ 1.21(6H, d, J=6.2 Hz), 1.56(4H, m), 2.03(6H, s), 4.87(2H, m); $^{13}C$ NMR $\delta$ 19.8, 21.1, 31.7, 70.5, 170.4; $[\alpha]_D^{21}-0.027$ (c 7.53, $CHCl_3$). Reduction with LAH gave (R,S)-2,5-dihydroxyhexane. bp 90°–100° C. (4 torr); $^1H$ NMR $\delta$ 1.18(6H, d, J=6.1 Hz), 1.55 (4H, m), 2.03(2H, s), 3.84(2H, m); $^{13}C$ NMR $\delta$ 25.2, 34.8, 67.6; $[\alpha]_D^{21}0°$ (c 8.06, $CHCl_3$). The bis-MTPA ester was 4% R,R, 92% R,S and 4% S,S.

EXAMPLE X

Ketone reduction with (R,R)-2,5-dimethylborolane

Treatment of alkyl ketones with (R,R)-2,5-dimethylborolane provided the corresponding alcohols with excellent enantioselection. The degrees of asymmetric induction (% e.e.) are 100 >95 and 76 for tertiery, secondary and primary alkyl groups, respectively, as exemplified in table II.

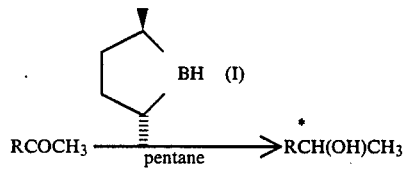

TABLE II

| R | temp (°C.) | yield | % ee | absolute configuration |
|---|---|---|---|---|
| ![isopropyl] | r.t. | 80 | 99.8 | S |
| ![cyclohexyl] | −20 | 70 | 95.5 | S |
| n-$C_6H_{13}$ | −30 | 72 | 85.0 | S |

EXAMPLE XI

The Aldol Reaction

Aldol reactions using the triflate (trifluoromethylsulfonate) (1c), derived from (R,R)-10 under the conditions specified below proceeded stereoselectively.

EXAMPLES

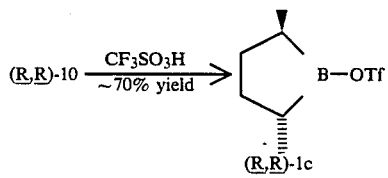

-continued

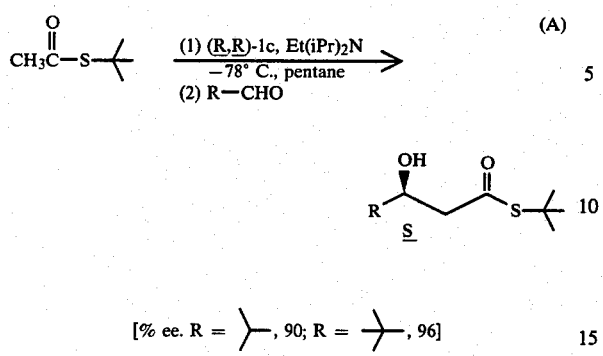

[% ee. R = ⟩—, 90; R = ⟩+, 96]

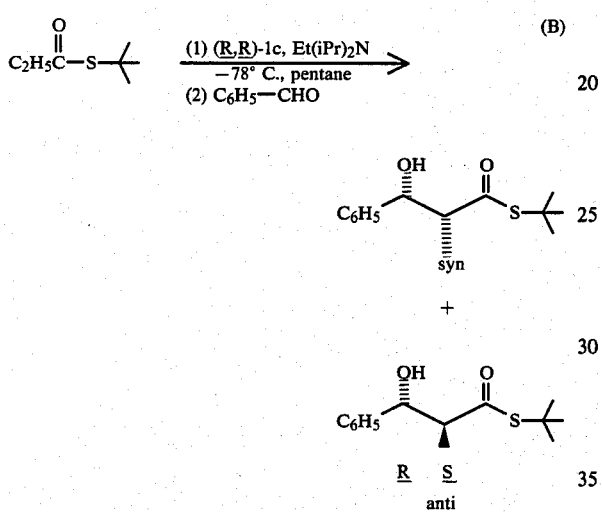

[yield 80%; syn/anti ratio, 1:>20; % ee of anti (2S, 3R), 99.1]

Note that Examples A and B are two types of enantio-selective transformations which are almost impossible with other aldol methods.

EXAMPLE XII

Carbonyl Addition Reaction

A typical example is shown below schematically.

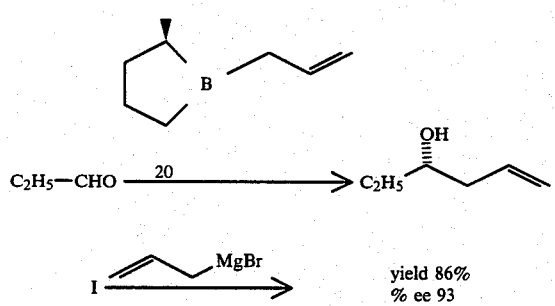

I claim:

1. A compound of the formula:

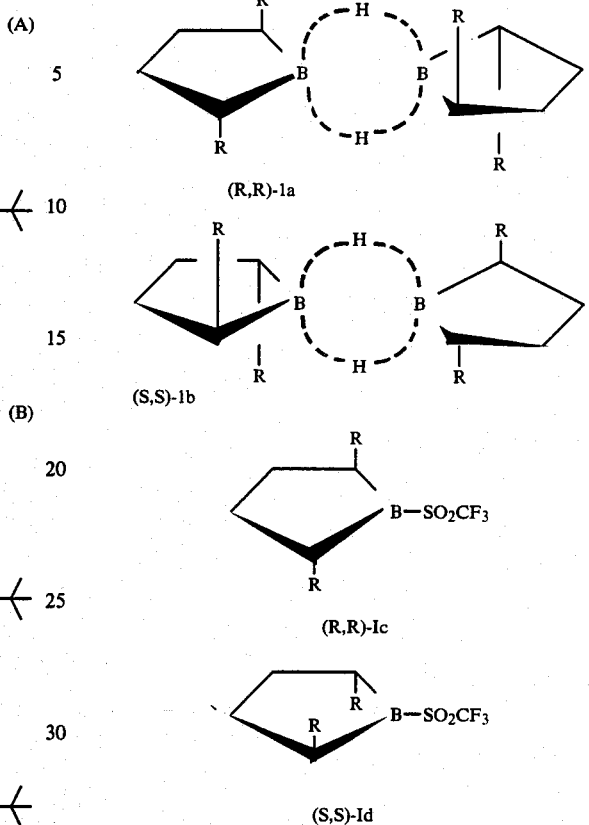

wherein R is a primary or secondary alkyl or trimethylsilyl group.

2. The compound of claim 1 having the structure of 1a wherein R is methyl.
3. The compound of claim 1 having the structure of 1b wherein R is methyl.
4. The compound of claim 1 having the structure of 1a wherein R is ethyl.
5. The compound of claim 1 having the structure of 1b wherein R is ethyl.
6. The compound of claim 1 having the structure of 1a wherein R is isopropyl.
7. The compound of claim 1 having the structure of 1b wherein R is isopropyl.
8. The compound of claim 1 having the structure of 1a wherein R is trimethylsilyl.
9. The compound of claim 1 having the structure of 1b wherein R is trimethylsilyl.
10. The compound of claim 1 having the structure of 1c wherein R is methyl.
11. The compound of claim 1 having the structure of 1d wherein R is methyl.
12. The compound of claim 1 having the structure of 1d wherein R is ethyl.
13. The compound of claim 1 having the structure of 1d wherein R is ethyl.
14. The compound of claim 1 having the structure of 1c wherein R is isopropyl.
15. The compound of claim 1 having the structure of 1d wherein R is isopropyl.
16. The compound of claim 1 having the structure of 1c wherein R is trimethylsilyl.
17. The compound of claim 1 having the structure of 1d wherein R is trimethylsilyl.

* * * * *